US012708349B2

(12) United States Patent
Yadavalli

(10) Patent No.: US 12,708,349 B2
(45) Date of Patent: Aug. 18, 2026

(54) SYSTEMS, METHODS, AND USER INTERFACES FOR DISPLAYING ULTRASOUND TESTING DATA

(71) Applicant: Baker Hughes Holdings LLC, Houston, TX (US)

(72) Inventor: Siva Sankar Yadavalli, Karnataka (IN)

(73) Assignee: Baker Hughes Holdings LLC, Houston, TX (US)

( * ) Notice: Subject to any disclaimer, the term of this patent is extended or adjusted under 35 U.S.C. 154(b) by 0 days.

(21) Appl. No.: 18/938,959

(22) Filed: Nov. 6, 2024

(65) Prior Publication Data

US 2026/0123919 A1 May 7, 2026

(51) Int. Cl.

| | |
|---|---|
| ***A61B 8/00*** | (2006.01) |
| ***G06F 3/04845*** | (2022.01) |
| ***G06F 3/04883*** | (2022.01) |
| ***G06T 11/60*** | (2006.01) |
| ***G06V 10/25*** | (2022.01) |

(52) U.S. Cl.
CPC .............. *A61B 8/58* (2013.01); *A61B 8/5215* (2013.01); *G06F 3/04845* (2013.01); *G06F 3/04883* (2013.01); *G06T 11/60* (2013.01); *G06V 10/25* (2022.01)

(58) Field of Classification Search
CPC ......... G01N 29/069; G01N 2291/0289; G01N 2291/0258; G01N 29/226; A61B 8/58; A61B 5/7425
See application file for complete search history.

(56) References Cited

U.S. PATENT DOCUMENTS

2021/0364472 A1* 11/2021 Jack .................. G01N 29/2456
2024/0280541 A1* 8/2024 Badeau ............. G01N 29/0645

* cited by examiner

*Primary Examiner* — Gerald Johnson
(74) *Attorney, Agent, or Firm* — Mintz, Levin, Cohn, Ferris, Glovsky and Popeo, P.C.

(57) ABSTRACT

Ultrasonic testing (UT) data acquired during an inspection of an object is received and a first image of a portion of the object is displayed. The first image is generated in a first scan type based on the UT data. A first user input characterizing a first modification of the first image to focus on a region of interest within the portion of the object can be received, and the first image can be updated based on the first modification. A second user input characterizing a switch from the first scan type to a second scan type can be received. A second image of the portion of the object that is generated in the second scan type can then be displayed. A second modification to the second image based on the first modification to display the region of interest within the portion of the object can be automatically applied.

20 Claims, 9 Drawing Sheets

SYSTEMS, METHODS, AND USER INTERFACES FOR DISPLAYING ULTRASOUND TESTING DATA

FIELD

The present disclosure relates generally to non-destructive testing, in particular to ultrasonic testing.

BACKGROUND

Ultrasonic testing (UT) is form of non-destructive testing that uses ultrasonic probes to transmit ultrasonic waves into an object being inspected and receive echoes that can be used to generate images of the object that can be inspected to detect flaws within the object. Data collected during UT can be acquired using a variety of scanning techniques that can be used to generate a series of images of the object. Several common scan types include Amplitude scans (A-Scans), Sectorial scans (S-Scans), Brightness or Cross-sectional scans (B-Scans) and Plan-View or Top-View scans (C-Scans). A-Scans can be acquired using an UT probe that sends an ultrasonic pulse into the object being inspected and receives echoes that can be displayed as a representation of the object in terms of amplitude of the echo at a time/depth within the object at a specific location. S-Scans can be acquired using an UT phased-array probe that sends an ultrasonic beam into the object being inspected and receives echoes that can be displayed as a representation of the object in terms of amplitude of the echo at a time/depth within the object at a location defined by the width of the beam. The ultrasonic beams can be transmitted into the object from a phased-array probe at a variety of beam angles/widths that can be chosen by the inspector based on the type of inspection being performed. B-Scans can be acquired by collecting a series of A-Scans or S-Scans at a plurality of locations along a linear path and compiling said scans to create a cross-sectional view of the object across the linear path that can be displayed as a two-dimensional representation of the object, showing amplitudes at a plurality of times/depths within the object at a plurality of locations along the path. C-Scans can be acquired by collecting an array of A-Scans or S-Scans over an area of the object in a grid-like pattern and compiling them to create a top-down view of the object that can be displayed as a more intuitive two-dimensional representation of the object, showing the internal geometry of the object. Inspectors can analyze these images to identify regions of interest in the object, for example regions containing a defect.

SUMMARY

In some aspects, the techniques described herein relate to a method including: receiving, by a computing device including a user interface display, at least one data processor, and a memory storing instructions, ultrasonic testing (UT) data acquired during an inspection of an object; displaying, on the user interface display, a first image of a portion of the object, wherein the first image is generated in a first scan type of a plurality of scan types based on the UT data; receiving, by the user interface display, a first user input characterizing a first modification of the first image to focus on a region of interest within the portion of the object; updating the first image based on the first modification; receiving, by the user interface display, a second user input characterizing a switch from the first scan type to a second scan type of the plurality of scan types; displaying, on the user interface display, a second image of the portion of the object, wherein the second image is generated in the second scan type; and automatically applying a second modification to the second image based on the first modification to display the region of interest within the portion of the object. The region of interest can be (for example) a structural defect in the object.

In one or more examples, the first scan type is an S-scan, and the first modification is a widening or narrowing of a beam angle of the S-scan corresponding to an increase or a decrease in a number of ultrasound beams of the S-scan that are shown in the first image. In other examples, the first scan type is a B-scan, and the first modification is a widening or narrowing of a cross-section of the B-scan corresponding to an increase or a decrease in a number of ultrasound beams of the B-scan that are shown in the first image. In other examples, the first modification is a navigation from a first portion of the portion of the object to a second portion of the portion of the object. In other examples, the first modification is a magnifying or de-magnifying of the first image.

The computing device can be a mobile device or any other suitable computing device. The user interface display can be a touchscreen display. Receiving at least one of the first user input or the second user input can include receiving a gestural input using the touchscreen display. The first user input can include a first gestural input and the second user input can include a second gestural input that is different from the first gestural input.

In other aspects, the techniques described herein relate to a system including: a user interface display; at least one data processor; and a memory storing instructions configured to cause the at least one data processor to: receive ultrasonic testing (UT) data acquired during an inspection of an object, display, on the user interface display, a first image of a portion of the object, wherein the first image is generated in a first scan type of a plurality of scan types based on the UT data, receive, by the user interface display, a first user input characterizing a first modification of the first image to focus on a region of interest within the portion of the object, update the first image based on the first modification, receive, by the user interface display, a second user input characterizing a switch from the first scan type to a second scan type of the plurality of scan types, display, on the user interface display, a second image of the portion of the object, wherein the second image is generated in the second scan type, and automatically apply a second modification to the second image based on the first modification to display the region of interest within the portion of the object. The region of interest can be (for example) a structural defect in the object.

The user interface display, the at least one data processor, and the memory can be components of a mobile device. In some implementations, the system further includes one or more UT probes for acquiring UT data.

In other aspects, the techniques described herein relate to a non-transitory computer readable storage medium storing instructions that, when executed by a data processor of a computing device including a user interface display, cause the data processor to: receive ultrasonic testing (UT) data acquired during an inspection of an object; display, on the user interface display, a first image of a portion of the object, wherein the first image is generated in a first scan type of a plurality of scan types based on the UT data; receive, by the user interface display, a first user input characterizing a first modification of the first image to focus on a region of interest within the portion of the object; update the first image based on the first modification; receive, by the user interface display, a second user input characterizing a switch from the first scan type to a second scan type of the plurality of scan types; display, on the user interface display, a second image of the portion of the object, wherein the second image is generated in the second scan type; and automatically apply a second modification to the second image based on the first modification to display the region of interest within the portion of the object.

The details of one or more variations of the subject matter described herein are set forth in the accompanying drawings and the description below. Other features and advantages of the subject matter described herein will be apparent from the description, the drawings, and the claims.

BRIEF DESCRIPTION OF THE FIGURES

The following description should be read in conjunction with the following figures. Like reference numerals across various drawings represent like elements.

DETAILED DESCRIPTION

Images of objects that are generated using the UT scan types described above are frequently displayed on a graphical user interface (GUI). However, assessing ultrasonic testing images using these GUIs can be difficult and time-consuming. For example, to view a particular region of interest of the object being inspected, a user is often required to manually input numerous parameters into the GUI. As a result, changing the displayed region of the testing object can be challenging. Moreover, each time the user switches from viewing the object under one scan type to another, the user may be required to repeat the process of manually defining a region of interest, which may prevent the user from efficiently assessing different views of the same region the object.

The systems, methods and computer readable storage media described herein advantageously enable users to efficiently navigate between different scans of an object being inspected without having to repeat the process of manually defining a region of interest. Specifically, the systems and methods described herein allow for a plurality of scan types of the object to be linked such that any modifications made by a user when viewing one scan type are automatically communicated across the other scan types. For example, a user can modify the displayed portion of the object to navigate to different portions of the object, zoom in/out to view smaller/larger areas of the displayed portion, or otherwise modify the view of the object in one scan type. As a result of this linking of the different scan types, once any modifications are made within the display of a first scan type, the user can switch view a second scan type and have the second scan type automatically displayed to view the portion, with the same zoom and with the same other modifications that were made when viewing the first scan type.

The user can search for a region of interest in the object by adjusting the displayed portion of an image of one scan type using gestural inputs such as pinching gestures or scrolling gestures. Once a region of interest has been identified, the user can use another gestural input (e.g., a finger swipe gesture) to switch to a different image showing a different scan type. When the user switches from the first scan type to the second scan type, the system can be configured to display a portion of the object within the image of the second scan type that directly corresponds to the region of interest that was identified in the previously viewed/modified image of the first scan type. This advantageously allows the user to efficiently and intuitively compare different views of the same region of the object without having to repeat the process of manually defining a region of interest.

Figure 1:
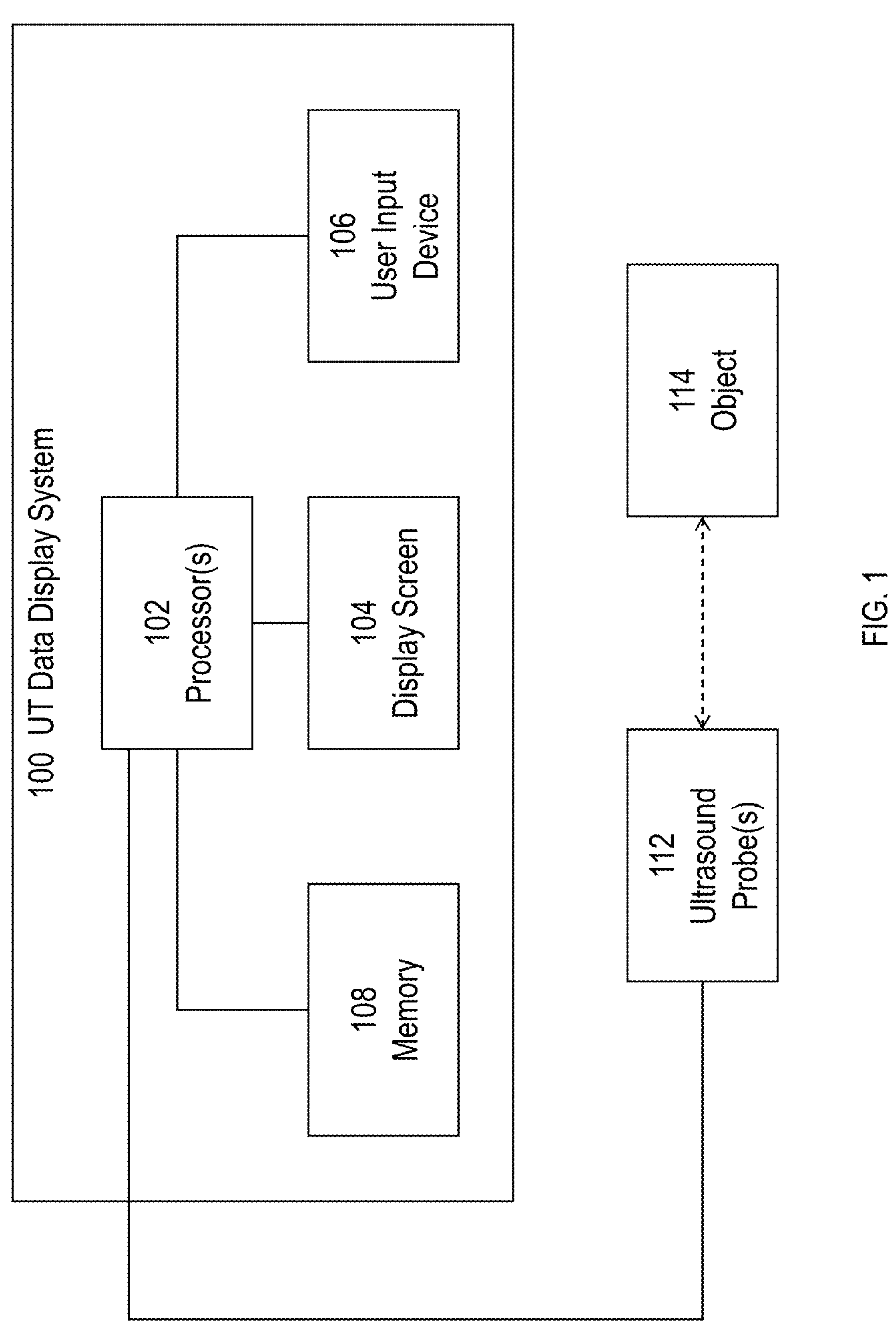
FIG. 1 is a block diagram illustrating one exemplary system for displaying ultrasonic testing data, according to some embodiments.

FIG. 1 is a block diagram of an exemplary system 100 for displaying ultrasonic testing (UT) data according to the systems and methods described herein. As shown in FIG. 1, system 100 can include one or more processors 102, a display screen 104, a user input device 106, and memory 108. System 100 can be implemented using any suitable device or combination of devices, for example a desktop computer, a laptop computer, or a mobile device such as a smart phone or a tablet.

Processor(s) 102 can include any suitable data processing device or combination of data processing devices, including (but not limited to) central processing unit(s) (CPU(s)), graphic processing unit(s) (GPU(s)), field programmable gate array(s) (FPGA(s)), or combinations thereof. Processor(s) 102 can be electrically coupled to memory 108, which can store instructions configured to be executed by processor(s) 102. Memory 108 can be or comprise any suitable type of digital data storage, for instance random access memory (RAM), a hard drive, a USB-drive, or the like.

In addition to memory 108, processor(s) 102 can be coupled to display screen 104. Display screen 104 can be a liquid crystal display (LCD), a light-emitting diode (LED) display, or any equivalent display device. When system 100 is in use, processor(s) 102 can be configured to display a graphical user interface (GUI) on display screen 104.

Processor(s) 102 can also be coupled to user input device 106. User input device 106 can be or comprise any suitable device for receiving user input, for example a keyboard, a mouse, a microphone, a button, or combinations thereof. In some embodiments, user input device 106 comprises a touch panel. The touch panel can be any suitable device for receiving user input through contact with the user's body (e.g., the user's finger). For example, the touch panel can be a resistive touch panel or a capacitive touch panel. In some embodiments, the touch panel is layered on top of an outer surface of display screen 104, i.e., in some embodiments, display screen 104 is a touchscreen.

A user of system 100 can interact with and manipulate the GUI displayed by processor(s) 102 on display screen 104 by providing inputs to user input device 106. For example, if user input device 106 includes a touch panel, a user can interact with and manipulate the GUI displayed by processor(s) 102 on display screen 104 by providing gestural inputs (e.g., tapping, swiping, pinching, etc.) to the touch panel. Gestural inputs to the touch panel can be detected and identified by processor(s) 102. In response to a given gestural input, processor(s) 102 can be configured to perform a specific action, for example changing or updating information displayed in the GUI.

System 100 can be used to view ultrasonic testing (UT) data that has been collected for an object 114. Ultrasonic testing can be performed to characterize or detect flaws within object 114. Object 114 can be any material, article, or entity that can be analyzed using ultrasonic testing techniques, for example a pipe for carrying oil or natural gas.

UT data can be received by processor(s) 102 from one or more ultrasonic probes 112 used to perform the testing. Testing can be executed using any suitable method, for example pulse-echo method, wherein a probe emits ultrasonic signals through a surface of an object 114 being tested and then detects the signals that are reflected back through the surface, or a through-transmission method, wherein one probe emits ultrasonic signals through one surface of object 114 and another probe detects the signals that pass through a second surface of object 114. In various embodiments, UT data collected by probe(s) 112 for object 114 can include measurements such as reflected signal intensity measurements, reflected signal arrival time measurements, and signal attenuation measurements.

Any suitable data transmission mechanism or technique can be employed to transfer UT data from probe(s) 112 to processor(s) 102. For instance, processor(s) 102 may be configured directly couple to one or more ultrasound probes 112 via wired connection (e.g., using one or more USB cables) or via a wireless connection (e.g., using Bluetooth or Wi-Fi). Alternatively, UT data may be uploaded by probe(s) 112 an intermediate source, such as a server or cloud storage, from which processor(s) 102 can download data. UT data received by processor(s) 102 can be stored in memory 108.

After receiving UT data from probe(s) 112, processor(s) 102 can generate one or more images of object 114 using the received UT data. Each image can correspond to a different view of object 114. For example, a first image can be an A-Scan/S-Scan view of object 114, a second image can be a B-Scan view of object 114 and a third image can be a C-Scan view of object 114.

When a user of system 100 wishes to inspect the UT data for object 114, processor(s) 102 can display one of generated images (i.e., one of the views) of object 114 in the GUI displayed on display screen 104. The user can change the displayed scan/view of object 114 by providing input to user input device 106, as described in greater detail below. Processor(s) 102 can identify the input provided by the user and update the displayed view accordingly.

Each image generated by processor(s) 102 using the received UT data can show a different view/scan type of object 114. Corresponding portions of different images may show the same region of object 114 from different views/scans. Processor(s) 102 can be configured to modify the portion of an image that is displayed in the GUI in response to various user inputs to user input device 106. For example, if user input device 106 includes a touch panel, when the user inputs a pinching gesture to the touch panel, processor(s) 102 may magnify or de-magnify the displayed image. Various images that can be displayed and modified within the GUI of the display screen 104 are described in greater detail below.

In some embodiments, processor(s) 102 are configured to display one or more numerical values associated with a displayed image portion. For example, processor(s) 102 may display the value of the maximum amplitude that was measured in the region of the object shown in a displayed image portion, as described in greater detail below. Processor(s) 102 can be configured to determine such values based on the received UT data or, alternatively, can receive such values from another source.

Figure 2:
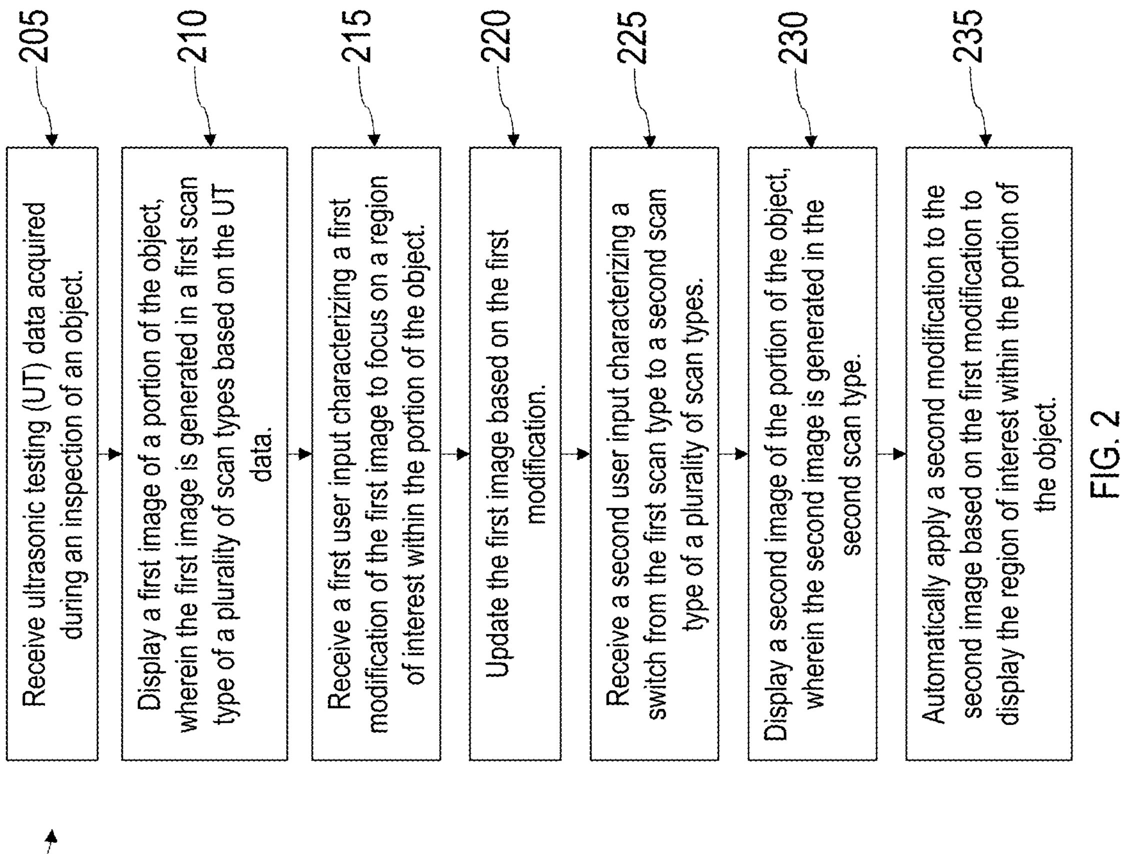
FIG. 2 is a flow diagram depicting one exemplary method for displaying ultrasonic testing data, according to some embodiments.

FIG. 2 provides a process flow diagram illustrating an exemplary method 200 for displaying UT data for an object. Method 200 can be executed by one or more processors of a system for displaying UT data, for example processor(s) 102 of system 100 shown in FIG. 1. Method 200 is intended only as an example; in some embodiments, a method for displaying UT data for an object may include steps that are not included in method 200, exclude steps that are included in method 200, or be executed in a different order than method 200.

At a step 205 of method 200, UT data acquired during an inspection of an object is received by the system. The UT data can be acquired using one or more ultrasound probes, for example probe(s) 112 described above with reference to FIG. 1. The UT data can be transmitted to the system via, e.g., a wired connection between the ultrasound probes and the system, a wireless connection between the ultrasound probes and the system, or other suitable data transmission mechanism.

At a step 210 of method 200, a first image of a portion of the object is displayed. The first image can be displayed using a user interface display such as display screen 104 of system 100 shown in FIG. 1. The first image can be generated in a first scan type of a plurality of scan types based on the UT data. Said plurality of scan types can include A-Scans, B-Scans, C-Scans, S-Scans, or combinations thereof. Accordingly, the first scan type in which the first image is generated can be, e.g., an A-Scan, a B-Scan, a C-Scan, or an S-Scan.

At a step 215 of method 200, a first user input characterizing a first modification of the first image to focus on a region of interest within the portion of the object is received. The first user input can be received by a user input device such as user input device 106 of system 100 shown in FIG. 1. In some implementations, the user interface display includes a touch panel (e.g., the user interface display is a touch screen display), so the first user input is received by the user interface display. If the user interface display includes a touch panel, then the first user input can be a gestural input such as a pinching gesture, a swiping gesture, a tapping gesture, or a scrolling gesture.

The first modification can include one or more changes to the first image. If, for example, the first scan type is an S-scan, the first modification can include a widening or narrowing of a beam angle of the S-scan corresponding to an increase or a decrease in a number of ultrasound beams of the S-scan that are shown in the first image. Similarly, if the first scan type is a B-scan, the first modification can include a widening or narrowing of a cross-section of the B-scan corresponding to an increase or a decrease in a number of ultrasound beams of the B-scan that are shown in the first image. The first modification can also include a navigation from a first portion of the portion of the object to a second portion of the portion of the object and/or a magnifying or de-magnifying of the first image.

The region of interest can depend on the object and the reasons for performing ultrasonic testing on the object. If, for example, the objective of the test is to identify structural defects or flaws in the object, the region of interest may be a potentially flawed or defective region that requires closer inspection. At a step 220 of method 200, the first image is updated based on the first modification to show the display the region of interest within the portion of the object.

At a step 225 of method 200, a second user input characterizing a switch from the first scan type to a second scan type of the plurality of scan types is received. Like the first user input, the second user input can be received by a user input device such as user input device 106 of system 100 shown in FIG. 1. In some implementations, the user interface display includes a touch panel (e.g., the user interface display is a touch screen display), so the second user input is received by the user interface display. If the user interface display includes a touch panel, then the second user input can be a gestural input such as a pinching gesture, a swiping gesture, a tapping gesture, or a scrolling gesture.

The second user input can be distinct from the first user input. For example, if the first user input includes a first gestural input and the second user input includes a second gestural input, the first gestural input may be different from the second gestural input.

The second scan type can be, e.g., an A-Scan, a B-Scan, a C-Scan, or an S-Scan and may be different from the first scan type. For example, if the first scan type is an S-Scan, the second scan type can be an A-Scan, a B-Scan, or a C-Scan.

At a step 230 of method 200, a second image of the portion of the object is displayed. Like the first image, the second image can be displayed using a user interface display such as display screen 104 of system 100 shown in FIG. 1. At a step 235 of method 200, a second modification is automatically applied to the second image to display the region of interest within the portion of the object. The second modification can be based on the first modification that updated the first image to focus on the region of interest.

Figure 3A:
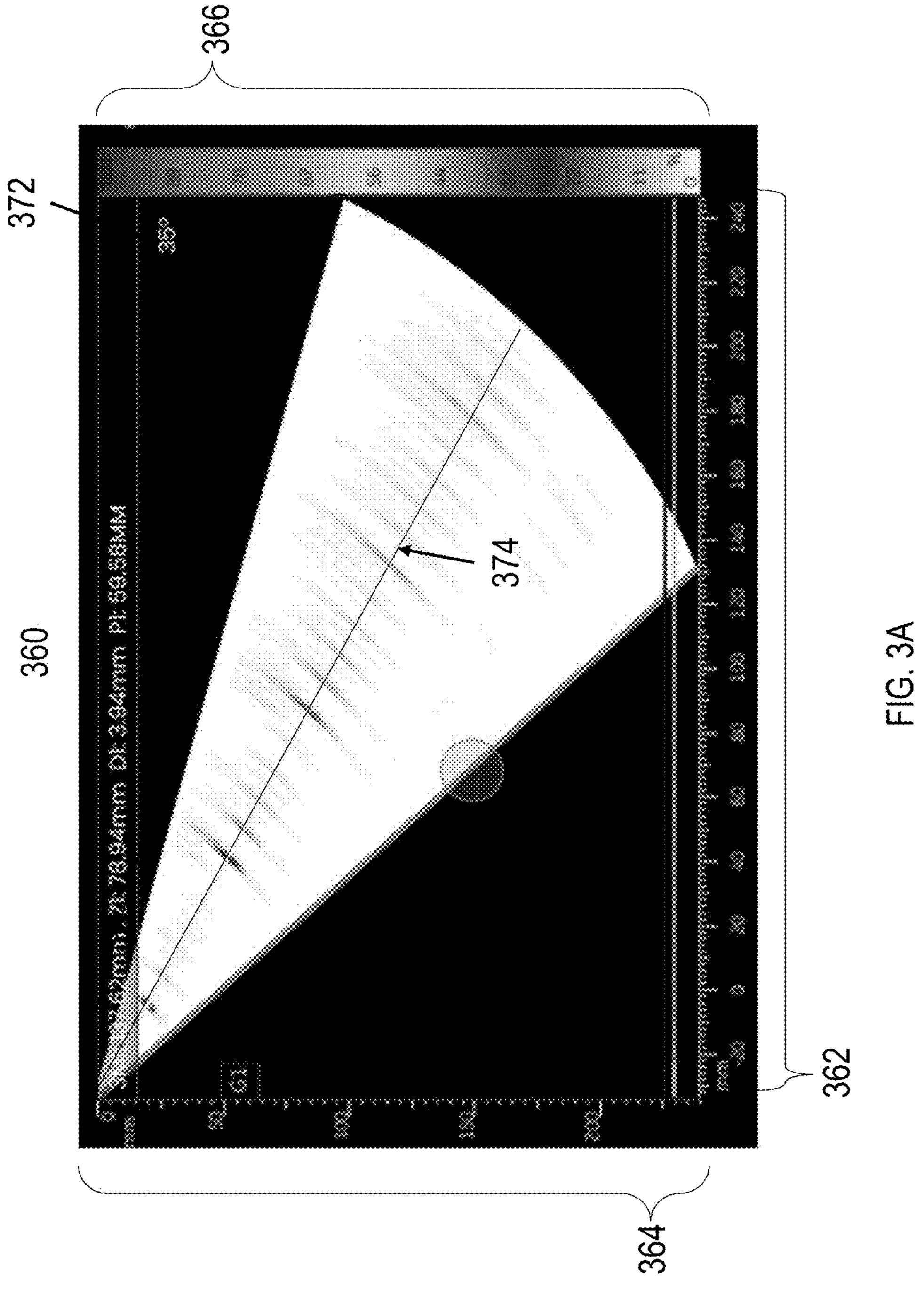
FIG. 3A shows an example user interface for displaying ultrasonic testing data, according to some embodiments.

FIG. 3A illustrates an exemplary GUI 360 for viewing UT data for an object being inspected. GUI 360 can be displayed on a display screen of a system for displaying UT data, for example display screen 104 of system 100 shown in FIG. 1. In this example, the GUI 360 is displaying an S-Scan view of an object. The displayed S-Scan view can include a horizontal axis 362 and a vertical axis 364. In some aspects, both the horizontal and vertical axes 362, 364 can include displayed units of length corresponding to horizontal and vertical positions, respectively, within a section of the object. The S-Scan view can also include a beam section 370 that can correspond to UT data acquired by a probe (e.g., probe(s) 112 of FIG. 1). The beam section 370 shows a sector region of the object across a beam angle 372 (e.g., 35° in this example). The beam section 370 is made up of a plurality of beams 374 that are acquired at different angles displayed on the screen. In some aspects, the beam section 370 can include visual representations of the ultrasonic signal intensity/amplitude at various locations in the object, which can be indicated using color scales which correspond to different amplitudes defined by an amplitude scale 366, as shown in FIG. 3A.

Depending on the region of interest, it may be desirable for the user to be able to widen or narrow the beam angle 372 of the beam section 370 to view wider or narrower regions of the object depicted by the UT data within the beam section 370. Accordingly, in some aspects, the user can interact with the GUI 360 to adjust the beam angle 372 of the beam section 370, as described below.

Figures 3B, 3C:
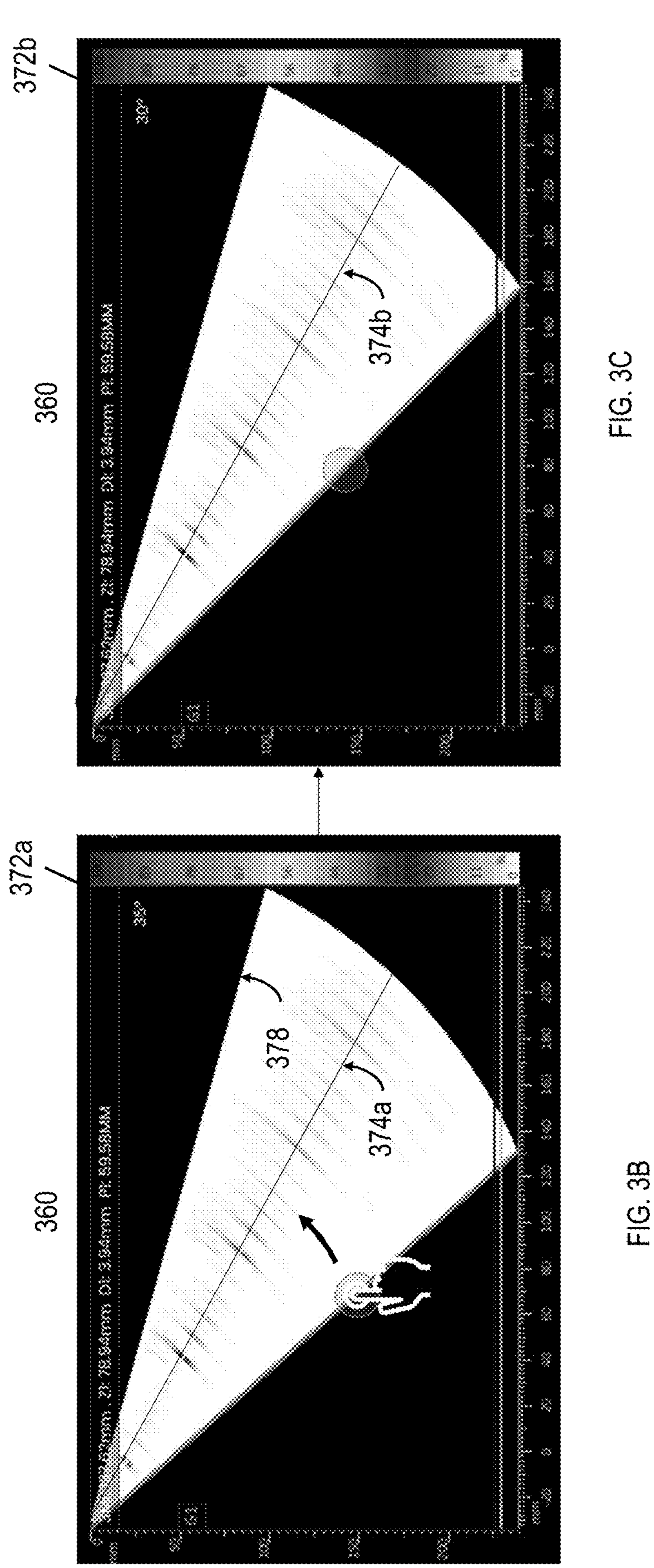
FIG. 3B shows an example user interaction with the user interface of FIG. 3A for modifying an image of an S-Scan view of an object, according to some embodiments.
FIG. 3C shows the user interface of FIG. 3B after the image of the S-Scan view is modified, according to some embodiments.

FIGS. 3B-3C illustrate an exemplary user interaction with GUI 360 for adjusting the displayed beam section 370 in a displayed S-Scan view of an object. As described above, GUI 360 can be displayed on a display screen of a system for displaying UT data, for example display screen 104 of system 100 shown in FIG. 1. In some aspects, the display screen (e.g., display screen 104 of system 100) can be a touch screen (e.g., of a smartphone or tablet or laptop or other device). Accordingly, in some aspects, the user can interact with GUI 360 by providing touch gestures to GUI 360. However, it is also realized that the display screen can be a traditional monitor type display and the user can interact with GUI 360 using a cursor controlled by a mouse or the like. In a case where the display screen is a touch screen, the user can modify the S-Scan view by providing touch gestures within the GUI 360.

As shown in FIG. 3B, the displayed beam section 370*a* is a portion of an image of an S-Scan view of an object that shows a first sector region of the object. In some embodiments, different gestural inputs cause changes to be made various parameters that define the displayed beam section 370*a* (e.g., a sector of object through which ultrasound signals were swept during testing). Accordingly, one parameter associated with the displayed portion can be a beam angle. A first beam angle 372*a* may be associated with displayed beam section 370*a*. The user may increase or decrease the first beam angle 372*a* by selecting, via a finger gesture 375, and dragging one or both edges 376, 378 of the beam section 370*a* to pull the edges apart or to push the edges together. For example, the user can select edge 376 of beam section 370*a* and push edge 376 toward edge 378 to decrease the beam angle 372*a* to a second beam angle 372*b* that defines a second beam section 370*b*, as shown in FIG. 3C. GUI 360 can be configured to display the beam angle value corresponding to the currently displayed beam section and may continuously update the angle value as changes are made to the beam angle.

Another parameter that can define the displayed portion of an S-Scan image is a number of ultrasound beams of the S-Scan that are displayed. As discussed above with reference to FIG. 3A, the beam section that is displayed in an S-Scan view of an object is made up of a plurality of beams 374. In an S-Scan view, increasing or decreasing beam angle of a displayed beam section as described above with reference to FIGS. 3B-3C can increase or decrease the number of ultrasound beams of the S-Scan that are displayed. For example, the displayed beam section 370*a* shown in FIG. 3B may be made up of a first number of beams 374*a*. When the user decreases the beam angle from the beam angle associated with section 370*a* to the beam angle associated with section 370*b* shown in FIG. 3C, the number of ultrasound beams may decrease from the first number of ultrasound beams 374*a* to a second number of ultrasound beams 374*b* that defines the second beam section 370*b* shown in FIG. 3C.

Figures 3D, 3E:
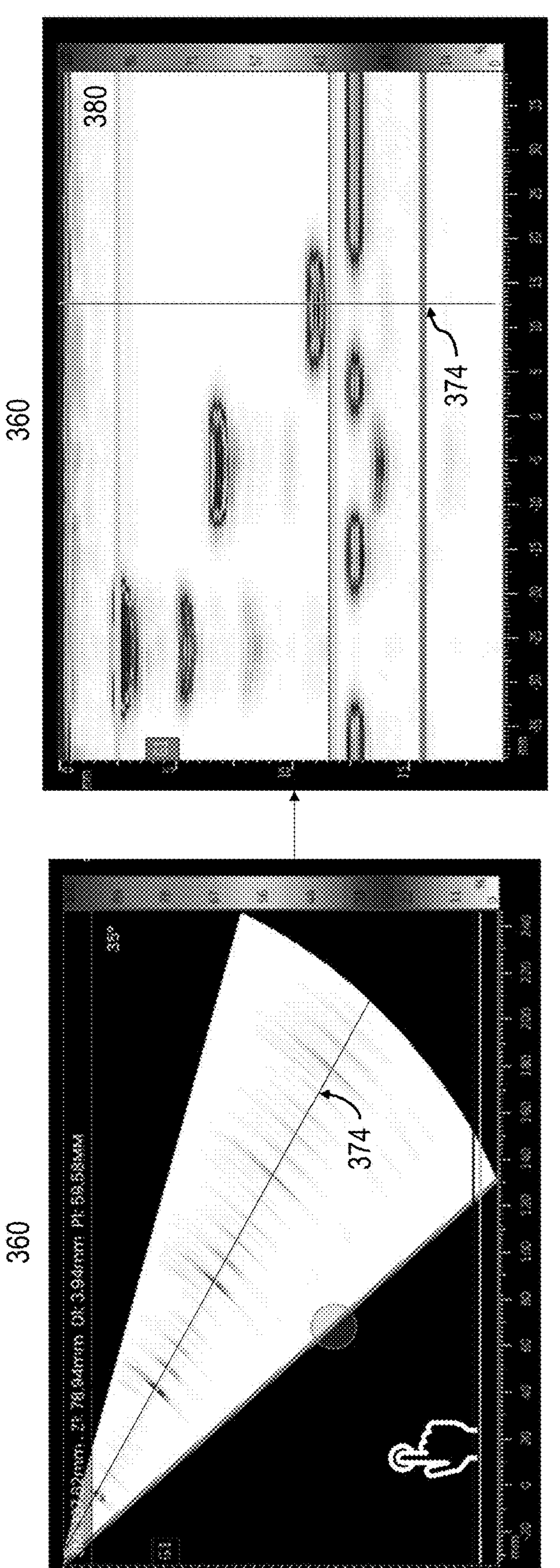
FIG. 3D shows an example user interaction with the user interface of FIG. 3A for switching between two UT scan types, according to some embodiments.
FIG. 3E shows the user interface of FIG. 3D after the UT scan type is switched, according to some embodiments.

FIGS. 3D-3E illustrate an exemplary user interaction with GUI 360 for switching the displayed scan/view of the object. In FIG. 3D, GUI 360 displays an S-Scan view of the object. As described in further detail above, the displayed beam section 370 shows a sector region of the object. In FIG. 3E, GUI 360 displays a B-Scan view of the object. The B-Scan view can include a displayed area 380 that shows a cross-sectional region of the object. The user can interact with GUI 360 to switch from the S-Scan view shown in FIG. 3D to the B-Scan view shown in FIG. 3E. For example, if the display screen on which GUI 360 is displayed (e.g., display screen 104 of system 100 shown in FIG. 1) is a touchscreen, the user can interact with GUI 360 to switch from the S-Scan view to the B-Scan view by providing a touch gesture 382 to GUI 360. For example, in some aspects, the gesture 382 can be a lateral swiping gesture provided by a finger of the user. However, it is also realized that the display screen can be a traditional monitor type display and the user can interact with GUI 360 to provide the gesture 382 using a cursor controlled by a mouse or the like. Responsive to the gesture 382, the system can be configured to replace the S-Scan view of the object with another view of the object (e.g., a B-scan or C-scan view). For example, as shown in FIGS. 3D-3E, responsive to the gesture 382, the GUI can be arranged to switch from showing the S-scan view of FIG. 3D, to show the B-scan view of FIG. 3E. To switch from the B-Scan view shown in FIG. 3E back to the S-Scan view shown in FIG. 3D, the user may provide an inverse finger gesture (e.g., a lateral swipe in the opposite direction to the lateral swipe provided to switch from the S-Scan view to the B-Scan view). Similar user inputs can be provided to switch between any two views/scans of the object. For example, to switch from the B-Scan view shown in FIG. 3E to, e.g., an A-Scan view of the object, the user may provide the same the finger gesture 382 that was provided to switch from the S-Scan view shown in FIG. 3D to the B-Scan view shown in FIG. 3E.

The systems described herein are able to link communicatively all of the various scan views of the object. Accordingly, when the user switches the displayed view/scan of an object within the GUI 360 from a first view/scan to a second view/scan, the region of the object that is shown in the second view/scan is automatically displayed in a way that corresponds to the region of the object that was shown in the first view/scan. For example, the sector region of the object shown by displayed beam section 370 in the S-Scan view provided in FIG. 3D can correspond to the cross-sectional region of the object shown by displayed area 380 in the B-Scan view provided in FIG. 3E. Any modifications to the image showing the first view/scan can be automatically carried over to the image showing the second view/scan when the user switches the displayed view. For instance, if the user adjusts the number of ultrasound beams in the plurality of beams 374 that make up the displayed beam section 370 while the image of the S-Scan view is displayed and then switches the displayed view/scan to the B-Scan view, modifications can be automatically applied to the B-Scan view so that the displayed area 380 is an area that is made up of the same plurality of beams 374 as the beam section 370.

Figures 3F, 3G:
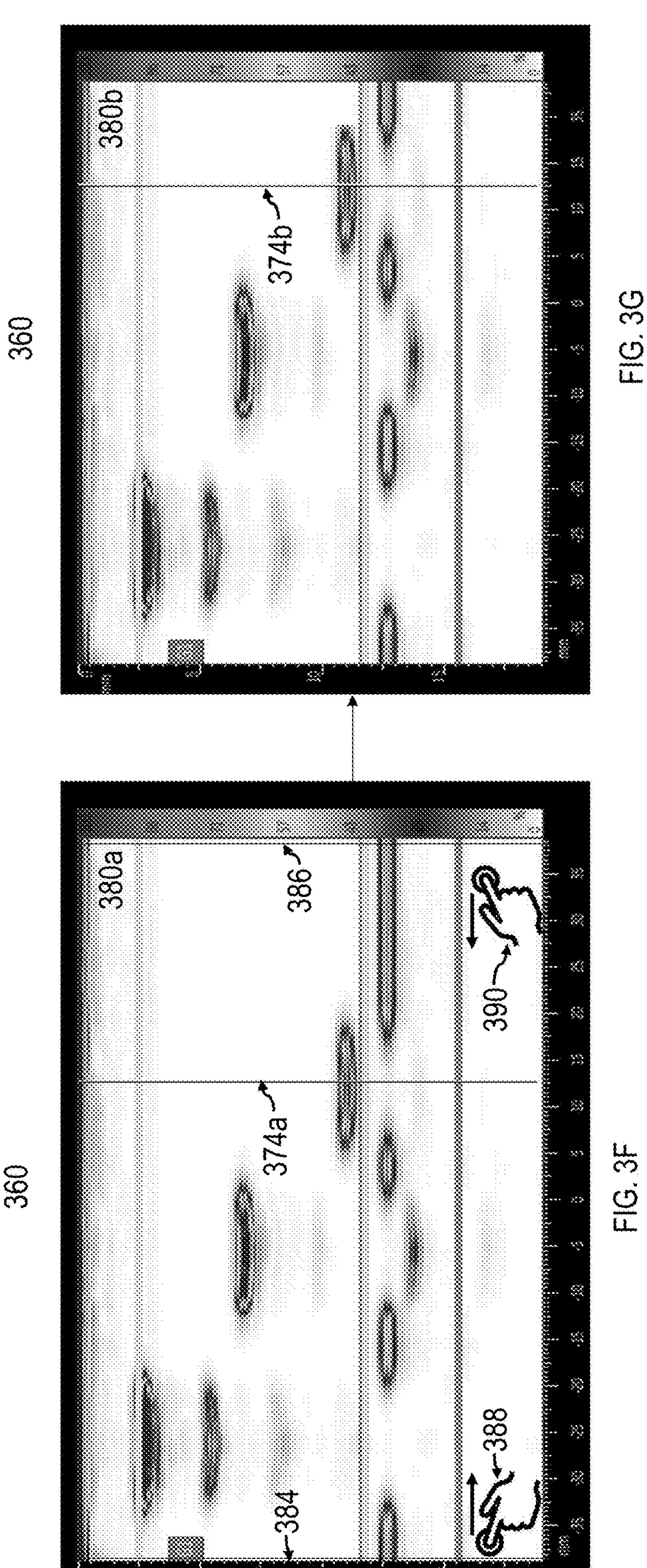
FIG. 3F shows an example user interaction with the user interface of FIG. 3A for modifying an image of a B-Scan view of an object, according to some embodiments.
FIG. 3G shows the user interface of FIG. 3F after the image of the B-Scan view is modified, according to some embodiments.

FIGS. 3F-3G illustrate an exemplary user interaction with GUI 360 for adjusting the displayed area 380 in a displayed B-Scan view of an object. In this example, the user can interact with GUI 360 by providing touch gestures to GUI 360. However, it is also realized that the display screen can be a traditional monitor type display and the user can interact with GUI 360 using a cursor controlled by a mouse or the like.

As shown in FIG. 3F, the displayed area 380*a* is a portion of an image of a B-Scan view of an object that shows a first cross-sectional region of the object. Different gestural inputs can cause changes to be made various parameters that define the displayed area 380*a*. One parameter that can define the displayed portion of a B-Scan image is a number of ultrasound beams. In a B-Scan view, increasing or decreasing the number of ultrasound beams can widen or narrow the displayed beam cross-section. The area 380*a* can be made up of a first plurality of beams 374*a*, as indicated in FIG. 3F. The user may change the number of ultrasound beams by selecting and dragging a first edge 384 of the displayed area 380*a* via a first finger gesture 388 and selecting and dragging a second edge 386 of the displayed area 380*a* via a second finger gesture 390 to pull the edges apart or to push the edges together. For example, the user can select edges 384, 386 of area 380*a* and pull edges 384, 386 away from one another to change the number of ultrasound beams from the first number of ultrasound beams 374*a* to a second number of ultrasound beams 374*b* that defines a second displayed area 380*b* shown in FIG. 3G.

Figures 3H, 3I:
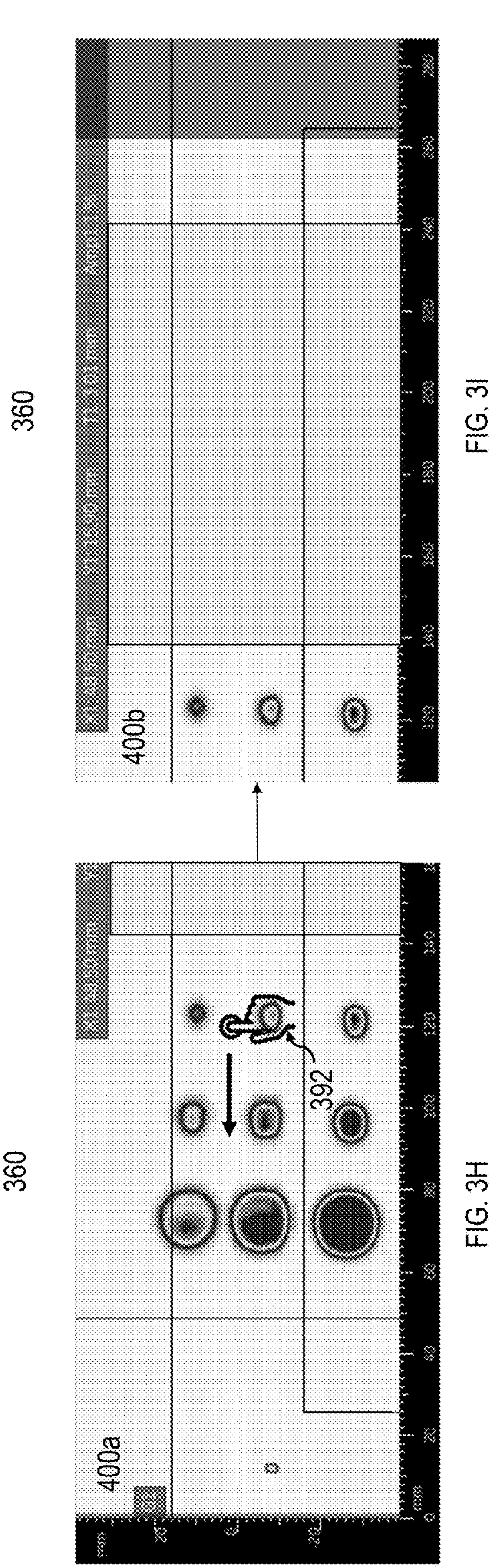
FIG. 3H shows an example user interaction with the user interface of FIG. 3A for navigating between different portions of an object, according to some embodiments.
FIG. 3I shows the user interface of FIG. 3H after the navigation is performed, according to some embodiments.

In some embodiments, GUI 360 allows the user to pan a displayed image to navigate to different portions of an object. FIGS. 3H-3I illustrate an exemplary user interaction with GUI 360 for panning across displayed image of an object. In this example, the user can interact with GUI 360 by providing touch gestures to GUI 360. However, it is also realized that the display screen can be a traditional monitor type display and the user can interact with GUI 360 using a cursor controlled by a mouse or the like.

In FIG. 3H, a first area 400*a* of an image of a C-Scan view of an object is displayed in GUI 360. In FIG. 3I, a second area 400*b* of the image of the C-Scan view of the object is displayed in GUI 360. The first displayed area 400*a* may show a top-down view of a first region of the object and the second displayed area 400*b* may show a top down-view of a second region of the object that is adjacent to the first region. The user can pan from the first displayed area 400*a* to the second displayed area 400*b* by scrolling, via a finger gesture 392, across the displayed image. The scrolling direction can depend on the relative locations of the first displayed area 400*a* and the second displayed area 400*b* in the image of the C-Scan view. In the example shown in FIGS. 3H-3I, the second displayed area 400*b* is located to the right of the first displayed area, so the scrolling direction is from right to left. In other cases, the second displayed area may be, e.g., above and to the left of the first displayed area, in which case the scrolling direction needed to switch from the first displayed area to the second displayed area may be, e.g., downwards and to the right.

The user may pan across an image of an object displayed in GUI 360 to locate a region of interest in the object. If the user modifies a displayed image of a first scan/view by panning to a region of interest (e.g., as discussed above with reference to FIGS. 3H-3I) and then switches the displayed image to a second scan/view (e.g., as discussed above with reference to FIGS. 3D-3E), the GUI can be configured to automatically apply a modification to the image of the second scan/view so that the region of interest is displayed in the image of the second scan/view.

Figures 3J, 3K:
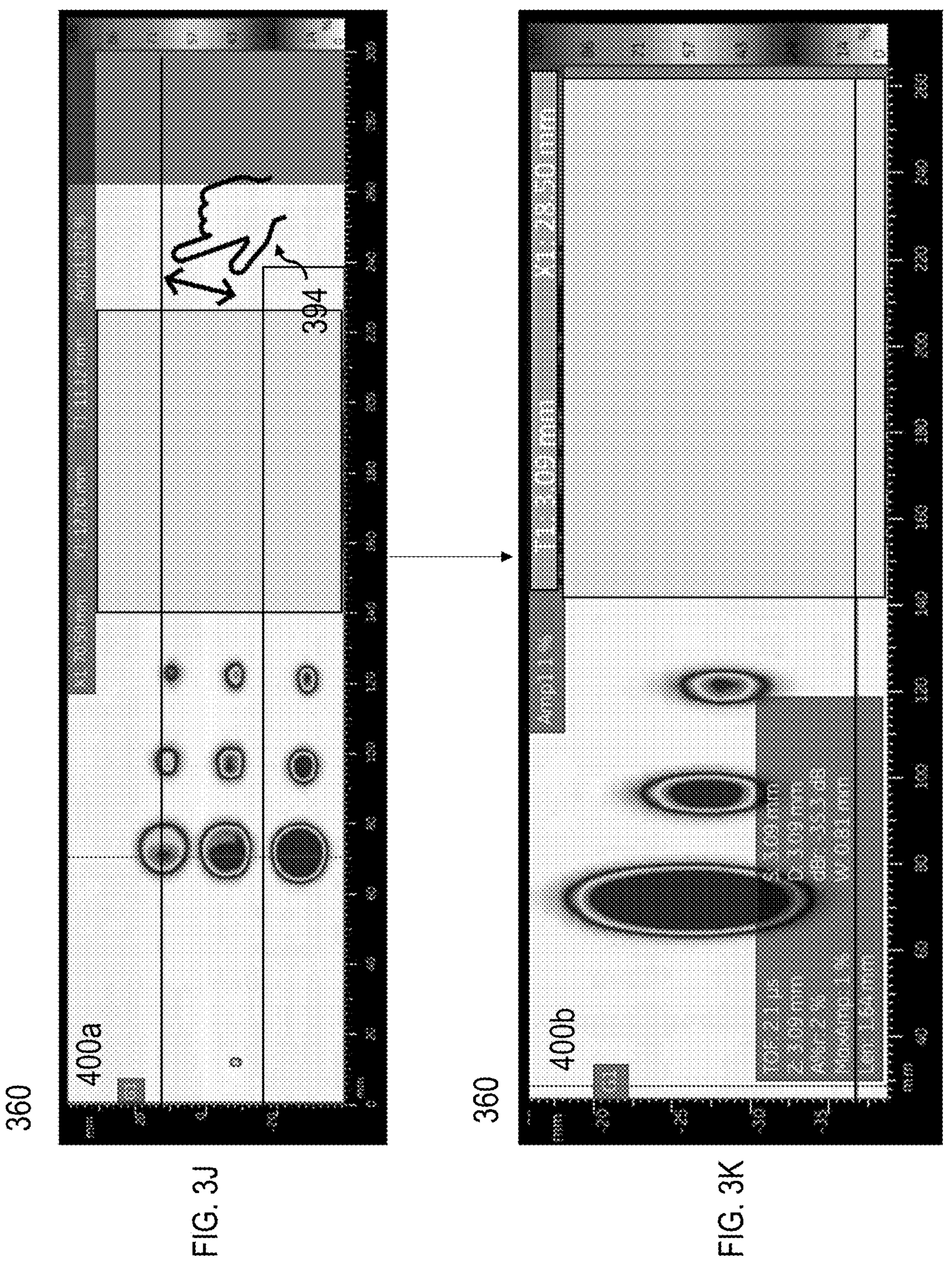
FIG. 3J shows an example user interaction with the user interface of FIG. 3A for magnifying a displayed image, according to some embodiments.
FIG. 3K shows the user interface of FIG. 3J after the displayed image is magnified, according to some embodiments.
Figures 3L, 3M:
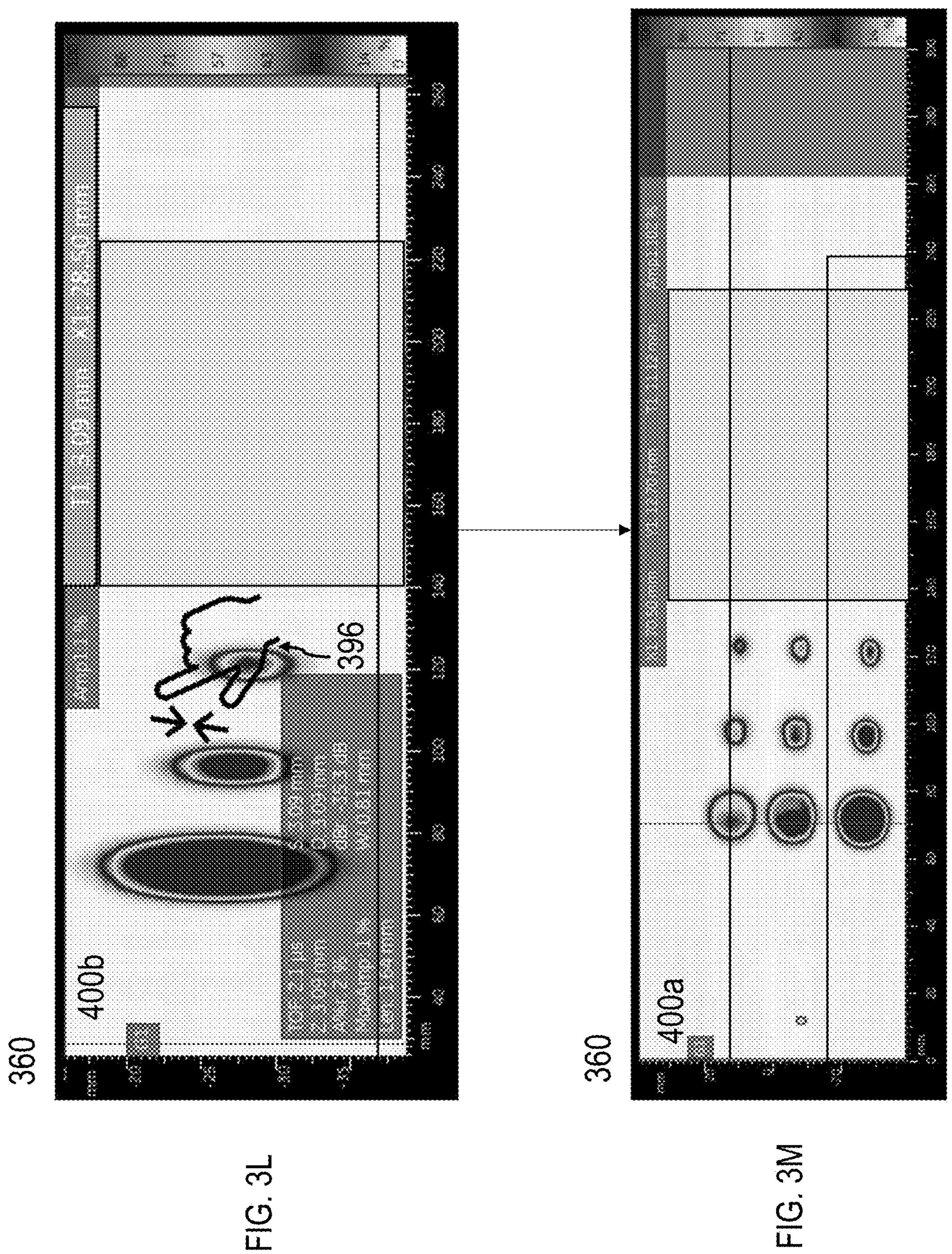
FIG. 3L shows an example user interaction with the interface of FIG. 3A for de-magnifying a displayed image, according to some embodiments.
FIG. 3M shows the user interface of FIG. 3L after the displayed image is de-magnified, according to some embodiments.

GUI 360 can also allow users to magnify or de-magnify a displayed image. FIGS. 3J-3K illustrate an exemplary user interaction with GUI 360 for magnifying a displayed image of an object and FIGS. 3L-3M illustrate an exemplary user interaction with GUI 360 for de-magnifying an image of an object. In these examples, the user can interact with GUI 360 by providing touch gestures to GUI 360. However, it is also realized that the display screen can be a traditional monitor type display and the user can interact with GUI 360 using a cursor controlled by a mouse or the like.

In FIG. 3J, a first area 400*a* of an image of a C-Scan view of an object is displayed in GUI 360. In FIG. 3K, a second area 400*b* of the image of the C-Scan view of the object is displayed in GUI 360. The first displayed area 400*a* is a top-down view of a first region of the object and the second displayed area 400*b* is a magnified top-down view of a second region of the object that is contained within the first region. The user can zoom in from the first displayed area 400*a* to the second displayed area 400*b* by providing a first finger gesture 394 to GUI 360. The first finger gesture 394 may be a pinch-out gesture. Similarly, as shown in FIGS. 3L-3M, the user can zoom out from the second displayed area 400*b* to the first displayed area 400*a* by providing a second finger gesture 396 to GUI 360. The second finger gesture 396 can be an inverse of the first finger gesture 394, for example a pinch-in gesture.

The user may magnify or de-magnify an image of an object displayed in GUI 360 to focus on a region of interest in the object. If the user modifies a displayed image of a first scan/view by magnifying or de-magnifying the image to display a region of interest (e.g., as discussed above with reference to FIGS. 3J-3M) and then switches the displayed image to a second scan/view (e.g., as discussed above with reference to FIGS. 3D-3E), the GUI can be configured to automatically apply a modification to the image of the second scan/view so that the region of interest is displayed in the image of the second scan/view.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. A method comprising:

receiving, by a computing device including a user interface display, at least one data processor, and a memory storing instructions, ultrasonic testing (UT) data acquired during an inspection of an object;

displaying, on the user interface display, a first image of a portion of the object, wherein the first image is generated in a first scan type of a plurality of scan types based on the UT data;

receiving, by the user interface display, a first user input characterizing a first modification of the first image to focus on a region of interest within the portion of the object;

updating the first image based on the first modification;

receiving, by the user interface display, a second user input characterizing a switch from the first scan type to a second scan type of the plurality of scan types;

displaying, on the user interface display, a second image of the portion of the object, wherein the second image is generated in the second scan type; and automatically applying a second modification to the second image based on the first modification to display the region of interest within the portion of the object.

2. The method of claim 1, wherein the first scan type is an S-scan, and the first modification is a widening or narrowing of a beam angle of the S-scan corresponding to an increase or a decrease in a number of ultrasound beams of the S-scan that are shown in the first image.

3. The method of claim 1, wherein the first scan type is a B-scan, and the first modification is a widening or narrowing of a cross-section of the B-scan corresponding to an increase or a decrease in a number of ultrasound beams of the B-scan that are shown in the first image.

4. The method of claim 1, wherein the first modification is a navigation from a first portion of the portion of the object to a second portion of the portion of the object.

5. The method of claim 1, wherein the first modification is a magnifying or de-magnifying of the first image.

6. The method of claim 1, wherein the user interface display is a touchscreen display, and receiving of the first user input comprises receiving a first gestural input within the first image of the portion of the object including at least one of a pinching gesture, a swiping gesture, a tapping gesture, or a scrolling gesture to focus on the region of interest within the portion of the object.

7. The method of claim 6, wherein the receiving the second user input comprises a receiving the second user input comprises receiving a second gestural input within the first image of the portion of the object including at least one of a pinching gesture, a swiping gesture, a tapping gesture, or a scrolling gesture to switch from the first scan type to the second scan type.

8. The method of claim 1, wherein the computing device is a mobile device.

9. The method of claim 1, wherein the region of interest comprises a structural defect.

10. A system comprising:

a user interface display;

at least one data processor; and a memory storing instructions configured to cause the at least one data processor to:

receive ultrasonic testing (UT) data acquired during an inspection of an object, display, on the user interface display, a first image of a portion of the object, wherein the first image is generated in a first scan type of a plurality of scan types based on the UT data, receive, by the user interface display, a first user input characterizing a first modification of the first image to focus on a region of interest within the portion of the object, update the first image based on the first modification, receive, by the user interface display, a second user input characterizing a switch from the first scan type to a second scan type of the plurality of scan types, display, on the user interface display, a second image of the portion of the object, wherein the second image is generated in the second scan type, and automatically apply a second modification to the second image based on the first modification to display the region of interest within the portion of the object.

11. The system of claim 10, wherein the first scan type is an S-scan, and the first modification is a widening or narrowing of a beam angle of the S-scan corresponding to an increase or a decrease in a number of ultrasound beams of the S-scan that are shown in the first image.

12. The system of claim 10, wherein the first scan type is a B-scan, and the first modification is a widening or narrowing of a cross-section of the B-scan corresponding to an increase or a decrease in a number of ultrasound beams of the B-scan that are shown in the first image.

13. The system of claim 10, wherein the first modification is a navigation from a first portion of the portion of the object to a second portion of the portion of the object.

14. The system of claim 10, wherein the first modification is a magnifying or de-magnifying of the first image.

15. The system of claim 10, wherein the user interface display is a touchscreen display, and the first user input comprises a first gestural input within the first image of the portion of the object including at least one of a pinching gesture, a swiping gesture, a tapping gesture, or a scrolling gesture to focus on the region of interest within the portion of the object.

16. The system of claim 15, wherein the second user input comprises a second gestural input within the first image of the portion of the object including at least one of a pinching gesture, a swiping gesture, a tapping gesture, or a scrolling gesture to switch from the first scan type to the second scan type.

17. The system of claim 10, further comprising one or more UT probes for acquiring UT data.

18. The system of claim 10, wherein the user interface display, the at least one data processor, and the memory are components of a mobile device.

19. The system of claim 10, wherein the region of interest comprises a structural defect.

20. A non-transitory computer readable storage medium storing instructions that, when executed by a data processor of a computing device comprising a user interface display, cause the data processor to:

receive ultrasonic testing (UT) data acquired during an inspection of an object;

display, on the user interface display, a first image of a portion of the object, wherein the first image is generated in a first scan type of a plurality of scan types based on the UT data;

receive, by the user interface display, a first user input characterizing a first modification of the first image to focus on a region of interest within the portion of the object;

update the first image based on the first modification;

receive, by the user interface display, a second user input characterizing a switch from the first scan type to a second scan type of the plurality of scan types;

display, on the user interface display, a second image of the portion of the object, wherein the second image is generated in the second scan type; and automatically apply a second modification to the second image based on the first modification to display the region of interest within the portion of the object.

* * * * *